US011103159B2

(12) United States Patent
Harshman et al.

(10) Patent No.: US 11,103,159 B2
(45) Date of Patent: Aug. 31, 2021

(54) EXHALED BREATH HYPOXIA BIOMARKERS

(71) Applicant: Government of the United States as Represented by the Secretary of the Air Force, Wright-Patterson AFB, OH (US)

(72) Inventors: Sean W. Harshman, Fairborn, OH (US); Brian A. Geier, Fairborn, OH (US); Claude C. Grigsby, Beavercreek, OH (US); Jeffrey B. Phillips, Centerville, OH (US); Darrin K. Ott, Waynesville, OH (US)

(73) Assignee: United States of America as represented by the Secretary of the Air Force, Wright-Patterson AFB, OH (US)

( * ) Notice: Subject to any disclaimer, the term of this patent is extended or adjusted under 35 U.S.C. 154(b) by 658 days.

(21) Appl. No.: 15/429,289

(22) Filed: Feb. 10, 2017

(65) Prior Publication Data

US 2017/0251952 A1 Sep. 7, 2017

Related U.S. Application Data

(60) Provisional application No. 62/303,826, filed on Mar. 4, 2016.

(51) Int. Cl.
*A61B 5/00* (2006.01)
*A61B 5/083* (2006.01)
(Continued)

(52) U.S. Cl.
CPC ............ *A61B 5/0833* (2013.01); *A61B 5/087* (2013.01); *A61B 5/0836* (2013.01);
(Continued)

(58) Field of Classification Search
CPC . A61B 5/0816; A61B 5/0205; A61B 5/02416; A61B 5/087; A61B 5/14551;
(Continued)

(56) References Cited

U.S. PATENT DOCUMENTS 3,395,701 A * 8/1968 Bartlett, Jr. ............ A62B 27/00
600/532
4,889,853 A * 12/1989 Tatsuoka ............... C07D 213/79
514/227.5
(Continued)

FOREIGN PATENT DOCUMENTS

WO 2009063226 5/2009

OTHER PUBLICATIONS

"Methodological and physiological aspects of exhaled breath analysis" PhD thesis: András Bikov (Year: 2013).*
(Continued)

*Primary Examiner* — May A Abouelela
(74) *Attorney, Agent, or Firm* — AFMCLO/JAZ; Chastity Whitaker

(57) ABSTRACT

A method of detecting hypoxia. Detecting hypoxia includes detecting, in exhaled breath, at least one indicator for hypoxia. The at least one indicator is selected from the group consisting of pentanal, 2-pentanone, 2-hexanone, 2-heptanone, 2-cyclopenten-1-one, and 4-butyrolactone.

12 Claims, 10 Drawing Sheets

(51) Int. Cl.

| | |
|---|---|
| *A62B 7/14* | (2006.01) |
| *A61B 5/087* | (2006.01) |
| *A61M 16/10* | (2006.01) |
| *A62B 9/00* | (2006.01) |
| *A61M 16/00* | (2006.01) |
| *A61B 10/00* | (2006.01) |

(52) U.S. Cl.
CPC .......... *A61M 16/024* (2017.08); *A61M 16/10* (2013.01); *A62B 7/14* (2013.01); *A62B 9/006* (2013.01); *A61B 2010/0087* (2013.01); *A61M 2016/0036* (2013.01); *A61M 2202/0208* (2013.01); *A61M 2205/3303* (2013.01); *A61M 2205/50* (2013.01); *A61M 2230/432* (2013.01); *A61M 2230/435* (2013.01)

(58) Field of Classification Search
CPC ..... A61B 5/4818; A61B 5/7282; A61B 5/097; A61B 5/0833; A61B 5/0836; A61B 2010/0087; A61M 15/0021; A61M 16/0069; A61M 16/0066; A61M 16/208; A61M 2016/0036; A61M 2016/1025; A61M 2202/0208; A61M 16/10; A61M 16/024; A61M 2230/432; A61M 2230/435; G16H 50/30; A62B 7/14
USPC ....... 600/531, 532, 543; 435/34, 125, 287.1; 422/84
See application file for complete search history.

(56) References Cited

U.S. PATENT DOCUMENTS

| | | | | |
|---|---|---|---|---|
| 6,165,105 | A * | 12/2000 | Boutellier | A63B 23/18 128/204.22 |
| 6,325,978 | B1 * | 12/2001 | Labuda | A61B 5/0833 422/84 |
| 6,726,637 | B2 * | 4/2004 | Phillips | A61B 5/097 600/529 |
| 7,008,380 | B1 * | 3/2006 | Rees | A61B 5/082 600/532 |
| 8,026,077 | B2 | 9/2011 | Madden | |
| 8,428,677 | B2 * | 4/2013 | Doyle | A61B 5/14551 600/323 |
| 9,678,058 | B2 * | 6/2017 | Rigas | G01N 33/497 |
| 10,401,318 | B2 * | 9/2019 | Rigas | G01N 27/126 |
| 2004/0162500 | A1 * | 8/2004 | Kline | A61B 5/412 600/532 |
| 2006/0185669 | A1 | 8/2006 | Bassovitch | |
| 2007/0003996 | A1 * | 1/2007 | Hitt | C12Q 1/04 435/34 |
| 2007/0077200 | A1 * | 4/2007 | Baker | A61M 16/12 424/9.1 |
| 2007/0129645 | A1 * | 6/2007 | Hartley | A61B 5/0809 600/532 |
| 2007/0167853 | A1 * | 7/2007 | Melker | A61M 16/026 600/532 |
| 2008/0213744 | A1 * | 9/2008 | Karlsson | A61B 5/412 435/2 |
| 2009/0024043 | A1 * | 1/2009 | MacLeod | A61M 16/0666 600/504 |
| 2009/0130138 | A1 * | 5/2009 | Stamets | A61P 31/12 424/195.15 |
| 2009/0239252 | A1 * | 9/2009 | Trevejo | C12Q 1/04 435/29 |
| 2010/0113539 | A1 * | 5/2010 | Scott | C07C 215/08 514/365 |
| 2010/0268105 | A1 * | 10/2010 | Feldman | A61B 5/0803 600/529 |
| 2010/0291617 | A1 * | 11/2010 | Trevejo | C12Q 1/04 435/34 |
| 2011/0143962 | A1 * | 6/2011 | Chaubron | C12Q 1/6886 506/16 |
| 2011/0269632 | A1 * | 11/2011 | Haick | B82Y 15/00 506/7 |
| 2012/0226168 | A1 * | 9/2012 | Osorio | A61B 5/4094 600/484 |
| 2012/0237968 | A1 * | 9/2012 | Rigas | G01N 33/497 435/34 |
| 2013/0060110 | A1 * | 3/2013 | Lynn | A61B 7/003 600/324 |
| 2013/0236980 | A1 * | 9/2013 | Moretti | G01N 21/783 436/133 |
| 2013/0252289 | A1 * | 9/2013 | Strobel | C12P 17/06 435/125 |
| 2013/0252313 | A1 * | 9/2013 | Strobel | C12P 17/06 435/254.1 |
| 2013/0303929 | A1 * | 11/2013 | Martino | A61B 5/097 600/532 |
| 2014/0094669 | A1 * | 4/2014 | Jaffe | A61M 16/0666 600/324 |
| 2014/0105824 | A1 * | 4/2014 | Shepard | G01N 33/566 424/9.2 |
| 2014/0105928 | A1 * | 4/2014 | Stamets | A61K 36/07 424/195.15 |
| 2014/0255970 | A1 * | 9/2014 | Prabhakarpandian | G01N 33/5029 435/29 |
| 2014/0364758 | A1 * | 12/2014 | Schindhelm | A61B 5/082 600/531 |
| 2014/0377285 | A1 * | 12/2014 | Liu | A61K 45/06 424/174.1 |
| 2015/0094219 | A1 * | 4/2015 | Trowell | C12Q 1/66 506/9 |
| 2015/0119742 | A1 * | 4/2015 | Tse | A61M 16/0493 600/531 |
| 2015/0134773 | A1 * | 5/2015 | Salem | G06F 19/3418 709/217 |
| 2015/0196245 | A1 * | 7/2015 | Peake | A61B 5/18 128/202.13 |
| 2015/0313506 | A1 * | 11/2015 | Borsari | A61B 5/742 600/532 |
| 2016/0022731 | A1 * | 1/2016 | Av-Gay | A61M 16/12 424/718 |
| 2016/0045161 | A1 * | 2/2016 | Alshaer | A61B 5/087 600/538 |
| 2016/0045527 | A1 * | 2/2016 | Bowden | A61K 31/35 514/23 |
| 2016/0113838 | A1 * | 4/2016 | Paydarfar | G16H 40/60 601/46 |
| 2016/0175623 | A1 * | 6/2016 | Alexander | A62B 7/14 434/262 |
| 2017/0020446 | A1 * | 1/2017 | Warren | A61B 5/0826 |
| 2017/0333708 | A1 * | 11/2017 | Conde | A61N 1/36 |
| 2018/0185522 | A1 * | 7/2018 | Davis | A61K 49/1863 |

OTHER PUBLICATIONS

R. Solberg et al., "Metabolomic analysis of plasma reveals new insights into asphyxia and resuscitation in pigs," PLoS ONE, vol. 5 (2010) e9606, 12 pages total.

B. J. Doleman et al., "Trends in odor intensity for human and electronic noses: Relative roles of odorant vapor pressure vs. molecularly specific odorant binding," PNAS, vol. 95 (1998) 5442-5447.

B. J. Doleman et al., "Comparison of odor detection thresholds and odor discriminabilities of a conducting polymer composite electronic nose versus mammalian olfaction," Sesnros and Actuators B, vol. 72 (2001) 41-50.

J-H Min et al., "Structure of an HIF-1a-pVHL comples: hydroxyproline recognition in signaling," Science, vol. 296 (2002) 1886-1889.

T. G. Smith et al., "The human side of hypoxia-inducible factor," British J Haemtaology, vol. 141 (2008) 325-334.

* cited by examiner

EXHALED BREATH HYPOXIA BIOMARKERS

Pursuant to 37 C.F.R. §1.78(a)(4), this application claims the benefit of and priority to prior filed co-pending Provisional Application Ser. No. 62/303,826, filed Mar. 4, 2016, which is expressly incorporated herein by reference in its entirety.

RIGHTS OF THE GOVERNMENT

The invention described herein may be manufactured and used by or for the Government of the United States for all governmental purposes without the payment of any royalty.

FIELD OF THE INVENTION

The present invention relates generally to biomarkers and, more particularly, to biomarkers for identifying hypoxia.

BACKGROUND OF THE INVENTION

It is known that the oxygen content of air decreases with elevation. As shown in FIG. 1, the partial pressure of oxygen ($PO_2$) at sea level is generally 160 mm Hg. At the peak of Everest (elevation of about 29,000 above sea level), the $PO_2$ drops to 53 mm Hg. Often at such elevations, climbers experience hypoxia, a condition in which the body is deprived of adequate oxygen supply. To combat hypoxia, climbers carry and use oxygen tanks.

Symptoms of hypoxia onset may include light-headedness, fatigue, numbness, and nausea. In extreme hypoxia, symptoms may include ataxia, hallucinations, headaches, papilledema, breathlessness, tachycardia, and pulmonary hypertension.

Pilots have reported experiencing in-flight hypoxic-like symptoms since the inception of high-altitude aviation (for example, altitudes of up to about 34,000 ft). Such an event poses an immediate threat to the pilot, the aircraft, and civilians on the ground. While pilots undergo extensive training to recognize and react to symptoms of hypoxia, research has shown that hypoxic episodes can adversely affect performance, even prior to loss of consciousness. Furthermore, the adverse reactions may persist for hours, even after the pilot has achieved adequate $O_2$ restoration.

Thus, there remains a need for methods of monitoring pilots, in-flight, for onset of hypoxic conditions.

Moreover, as the identification of volatile organic compounds ("VOCs") in exhaled breath ("EB") as disease biomarkers has been pursued for decades, it would be further advantageous to identify VOCs in EB associated with onset of hypoxia and utilize such VOC correlations with the early detection of hypoxia.

SUMMARY OF THE INVENTION

The present invention overcomes the foregoing problems and other shortcomings, drawbacks, and challenges of identifying hypoxia during high-altitude flight. While the invention will be described in connection with certain embodiments, it will be understood that the invention is not limited to these embodiments. To the contrary, this invention includes all alternatives, modifications, and equivalents as may be included within the spirit and scope of the present invention.

According to an embodiment of the present invention, a method of detecting hypoxia includes detecting, in exhaled breath, at least one indicator for hypoxia. The at least one indicator is selected from the group consisting of pentanal, 2-pentanone, 2-hexanone, 2-heptanone, 2-cyclopenten-1-one, and 4-butyrolactone.

Other embodiments of the present invention are directed to a method of detecting hypoxia in a pilot flying at high-altitude by monitoring the exhaled breath of the pilot. If at least one indicator for hypoxia, selected from the group consisting of pentanal, 2-pentanone, 2-hexanone, 2-heptanone, 2-cyclopenten-1-one, and 4-butyrolactone, is detected, then a flow of oxygen to the pilot is increased.

Still other embodiments of the present invention include a flight mask having an inhalation valve port, an exhalation valve port, and an air flow path extending between the inhalation valve port and the exhalation valve port. An exhaled breath sensor along the air flow path is configured to detect at least one of pentanal, 2-pentanone, 2-hexanone, 2-heptanone, 2-cyclopenten-1-one, and 4-butyrolactone.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Figure 2:
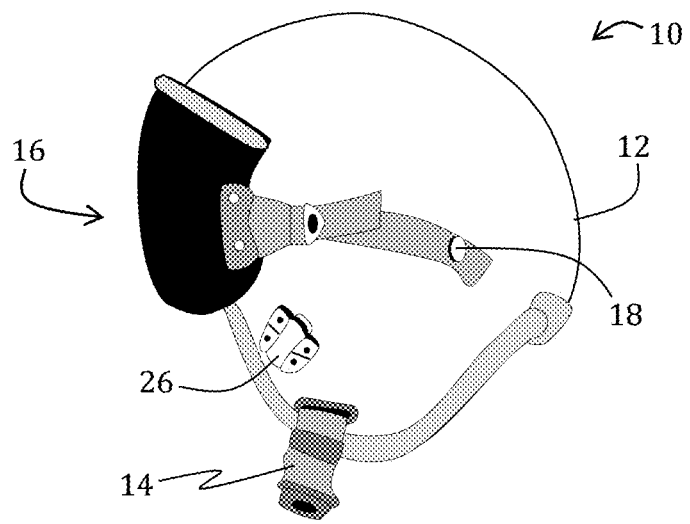
FIG. 2 is a side elevation view of an exemplary aviation helmet suitable for use with embodiments of the present invention.

Referring now to the figures, and in particular to FIG. 2, an aviation helmet suitable for use at ultra-high altitudes, for example, 34,000 ft, is shown. One exemplary, commercially-available helmet system 10 is the HGU-55/P Fixed Wing Aircrew Helmet System (Gentex, Corp., Carbondale, Pa.), which may include a helmet 12 configured to surround the pilot's head (not shown), a chin strap 14 configured to secure the helmet 12 about the pilot's head at the chin, and a retractable visor 16 assembly configured to rotate about a pivot point 18 on the helmet from a retracted position (not shown) to an deployed position (illustrated in FIG. 2) to shield the pilot's eyes.

Figure 1:
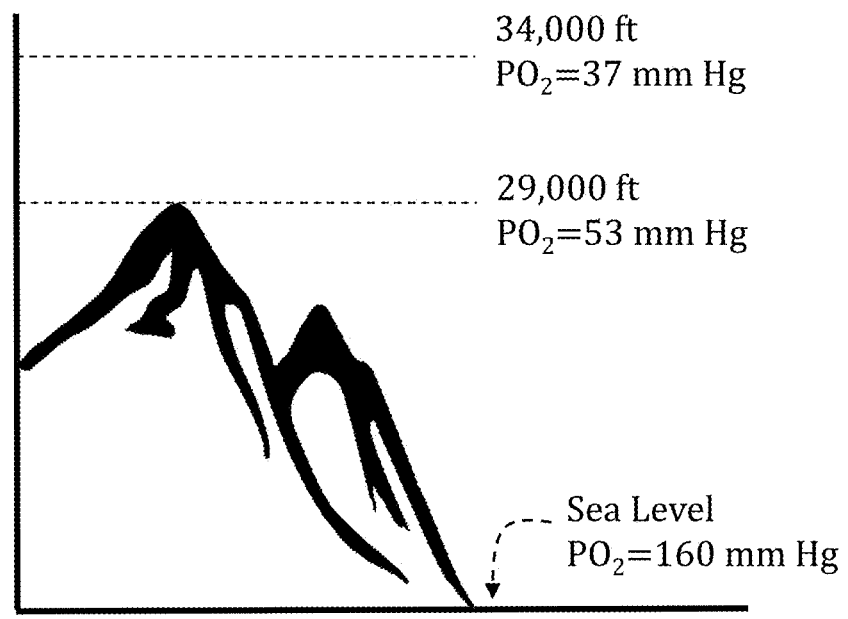
FIG. 1 is a schematic illustrating the relationship between elevation and partial pressure of oxygen.
Figure 3:
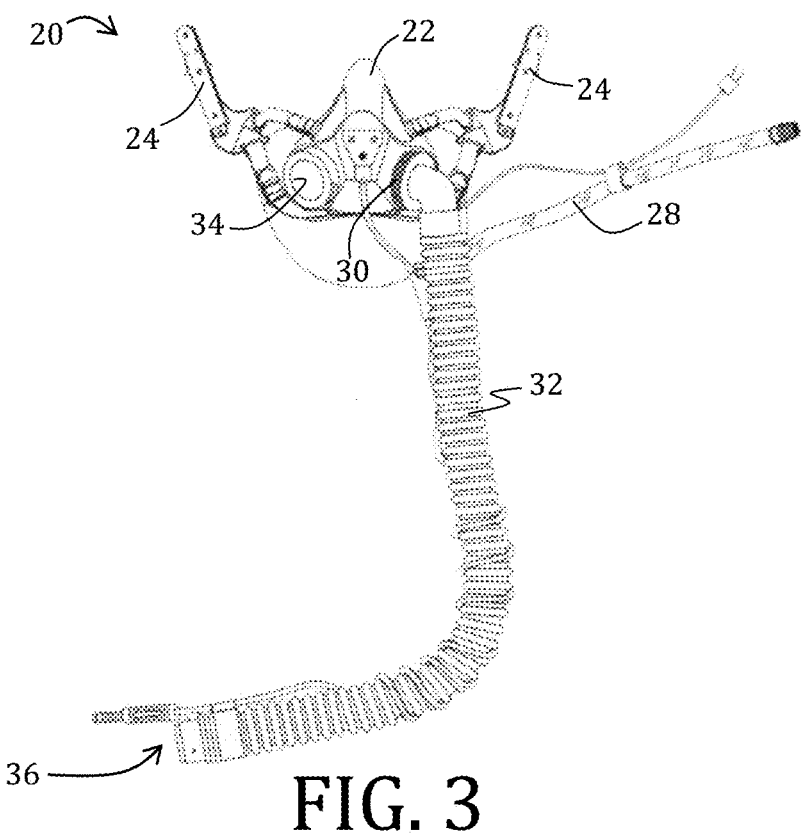
FIG. 3 is a front elevation view of an exemplary High Altitude Low Profile oxygen mask system suitable for use with the aviation helmet of FIG. 2 and with embodiments of the present invention.

The helmet of FIG. 2 is generally used with an oxygen mask system 20, such as the commercially-available MBU-20/P Combat Edge HALP (High Altitude Low Profile) HALP oxygen mask system illustrated in FIG. 3. Such oxygen mask systems 20 may include molded body 22 with a mask bayonet assembly 24 for connecting the molded body 22 to the helmet 10 and couplers 26 (FIG. 1). A quick disconnect strap 28 extends away from the molded body 22 and is configured to permit the pilot to pull the mask system 20 away quickly, such as in an emergency. The molded body 22 further includes two valved ports—an inhalation valve port 30 operably coupled to a breathing hose 32 and an exhalation valve port 34.

The breathing hose 32 extends from the inhalation valve port 30 to a connector 36 that is configured to be coupled to an oxygen source (not shown). Accordingly, and during in-flight maneuvers, oxygen may flow from the oxygen source (not shown), through the breathing hose 32, the inhalation valve port 34, and to the pilot. On exhalation, air moves from the pilot, through an exhalation valve 38 within the exhalation valve port 34, and into the cockpit atmosphere.

Figure 4:
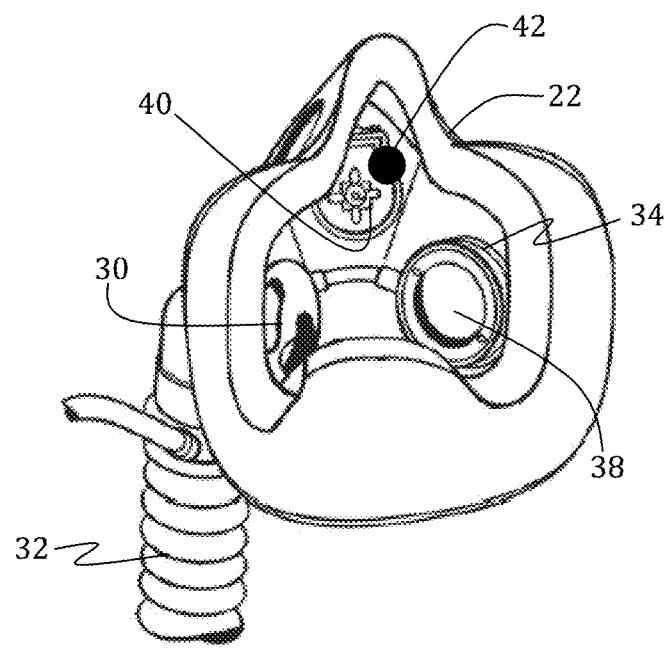
FIG. 4 is an elevation view of a revise side of a molded body of the oxygen mask system of FIG. 3.

In FIG. 4, a reverse side of the molded body 22 is shown and, in the illustrated embodiment, includes a microphone 40 so that the pilot may be in communication with a co-pilot, a wingman, or his command.

As was noted above, during ultra-high altitude flight pilots are at a higher risk for hypoxia. Six VOCs are associated with onset of hypoxia in EB, including: pentanal, 2-pentanone, 2-hexanone, 2-heptanone, 2-cyclopenten-1-one, and 4-butyrolactone. Therefore, monitoring of one or more of these VOCs, hereafter referred to as "indicators," would be beneficial in detecting hypoxia. As such, an EB sensor 42, according to one embodiment of the present invention, may be positioned and configured to detect the presence of at least one indicator in the pilot's EB.

Figure 5:
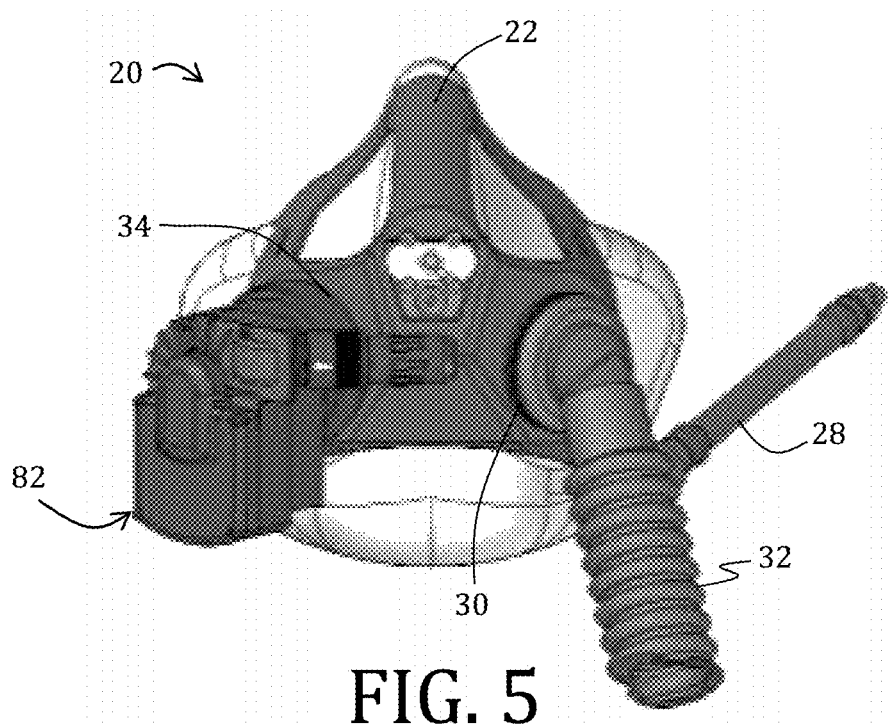
FIG. 5 is a front elevation view of an exemplary oxygen mask system having an exhalation sensor according to an embodiment of the present invention.
Figure 6:
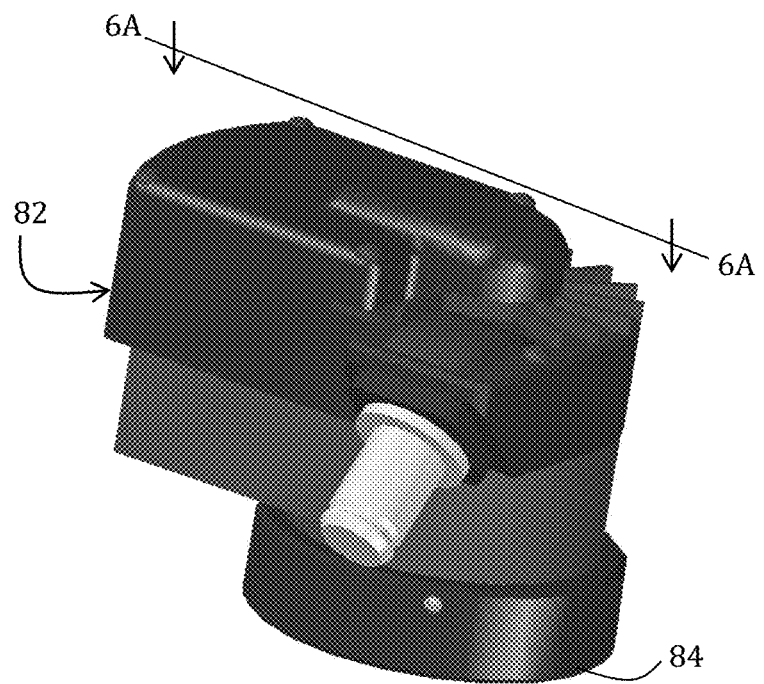
FIG. 6 is a side elevational view of the exhalation sensor illustrated with the oxygen mask system in FIG. 5.

Referring now to FIGS. 5 and 6, the oxygen mask system 20 is shown with an exhalation sensor 82 configured to be operably coupled the exhalation valve port 34 via a gasket 84. Details of the exhalation sensor 82 are shown in the cross-sectional view of FIG. 6A, which is taken along the line 6A-6A in FIG. 6.

Figure 6A:
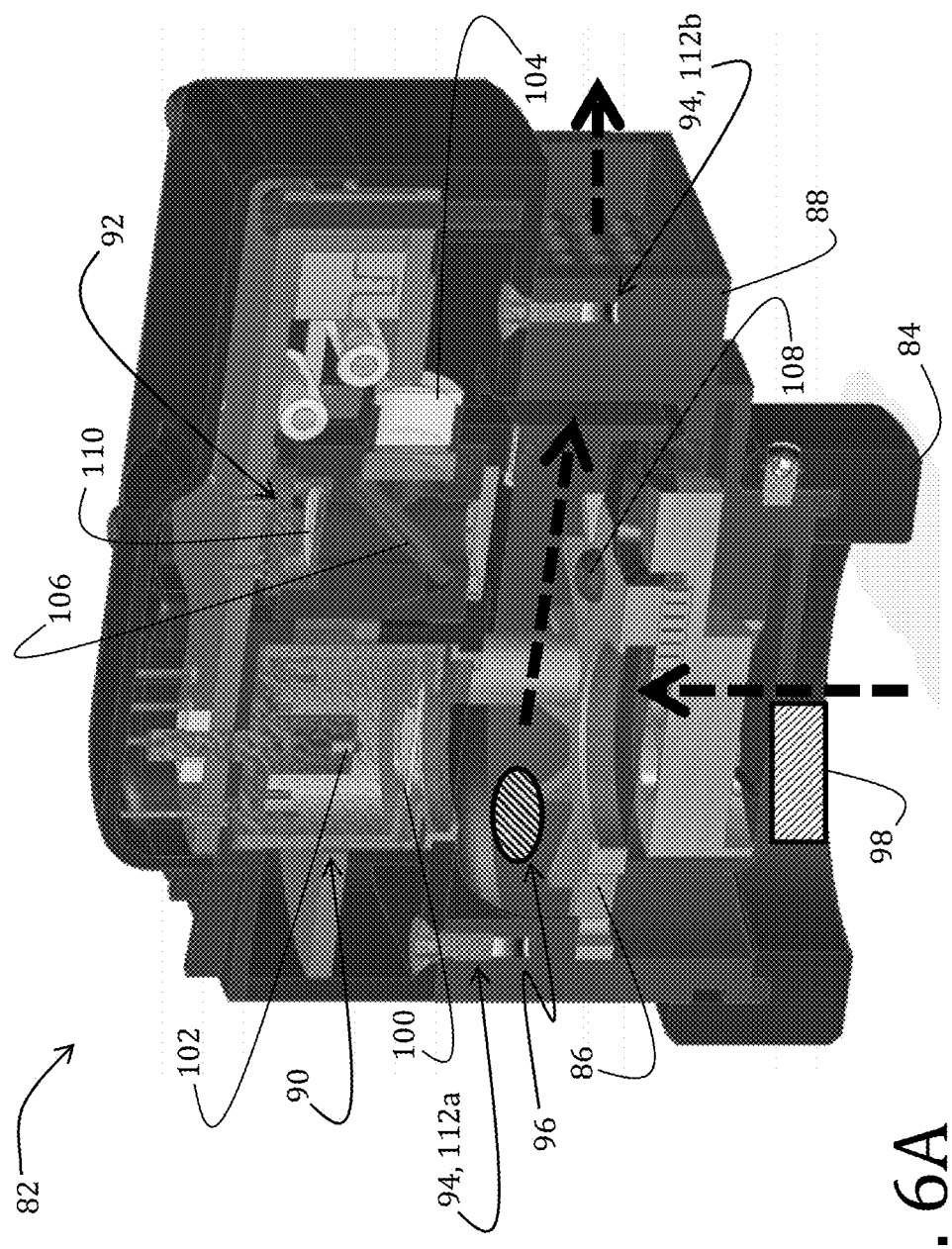
FIG. 6A is a cross-sectional view of the exhalation sensor taken along the line 6A-6A in FIG. 6.

EB flow, shown in FIG. 6A as embolden, dashed lines, moves from the exhalation valve port 34 (FIG. 5) of the oxygen mask system 20 (FIG. 5) by way of the gasket 84 and through a heating element 86, which may be configured to slightly elevate a temperature of the EB so as to reduce condensation within the exhalation sensor 82. Once warmed, the EB is deflected toward a vent 88. A carbon dioxide sensor 90, an oxygen sensor 92, a mass flow sensor 94, an EB sensor 96 (according to another embodiment of the present invention), or a combination thereof may be positioned along an air flow path extending between the gasket 84 and the vent 88 of the exhalation sensor 82.

The illustrative carbon dioxide sensor 90 of FIG. 6A is a nondispersive, infrared carbon dioxide detector comprising an infrared light source (approximate location shown indicated by a box 98; commercially-available products may include, for example, an LED from Boston Electronics Corp., Brookline, Mass.), a chromatic filter lens 100 (such as those commercially-available from Semrock, Inc. Rochester, N.Y.), and an infrared sensor 102 (here, a photodiode from Boston Electronics Corp.) positioned opposite the air flow path with respect to the lens 100. While those of ordinary skill in the art will readily understand implementation of alternative carbon dioxide sensors in a similar manner, the illustrated embodiment operates by emitting infrared light from the light source 98. Carbon dioxide molecules within the air flow path absorb certain wavelengths of infrared light ($\lambda$ being approximately 4.26 μm). A detected decrease in absorption within the infrared wavelengths associated with carbon dioxide (relative to a reference absorption) indicates a qualitative presence of carbon dioxide and may be used to quantitatively determine an amount of carbon dioxide present within the EB along the air flow path.

In the particular, illustrated embodiment, the oxygen sensor 92 is downstream from the carbon dioxide sensor 90 and comprises a light source 104 (emitting blue, visible spectrum wavelengths), a diachromatic lens 106, a fluorescent material 108 comprising a ruthenium complex, and a fluorescent detector 110, such as those available from Orbital Research, Inc. (Cleveland, Ohio). While those of ordinary skill in the art will readily understand implementation of alternative oxygen sensors in a similar manner, the illustrated embodiment operates by exciting the fluorescent material 108 via the light source 104. The fluorescent material 108 emits a red luminescence, the intensity and life-time of which being dependent on an amount of oxygen present within the EB along the air flow path. At the diachromatic lens 106, light having wavelengths within the blue visible spectrum are reflected while light having wavelengths within the red visible spectrum pass through the diachromatic lens 106 and are received by the fluorescence detector 110.

Referring still to FIG. 6A, the illustrative mass flow detector 94 comprises two mass flow sensors 112a, 112b positioned such that a first mass flow sensor 112a is upstream from a second mass flow sensor 112b. Thus positioned, a pressure differential measured by the flow sensors 112a, 112b may be determined. One suitable mass flow sensor may include those from Honeywell (Freeport, Ill.), including the 26PC or the Trustability SSC series.

Figure 6B:
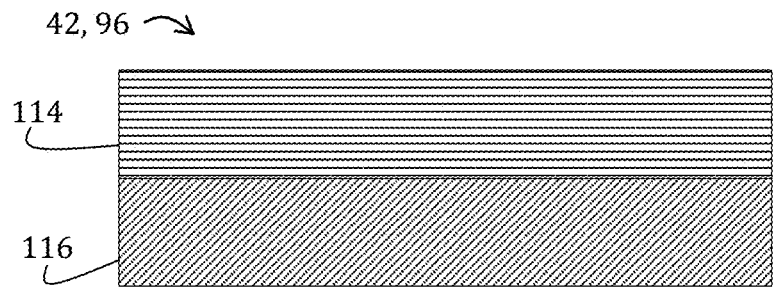
FIG. 6B is a cross-sectional view of a sensing material suitable for an exhalation sensor and according to an embodiment of the present invention.

The EB sensor 42, 96, according to some embodiments of the present invention and as illustrated in FIG. 6B, may comprise a sensing material 114 configured to have an affinity to polar molecules, such as alcohol, water, and the indicators. In construction, the sensing material may be a poly-vinylpyrrolidone ("PVP") or a PVP-polystyrene bend (which has a greater affinity for volatile forms of indicators). In other embodiments, still greater affinity for the indicators may be achieved by way of a molecular imprint polymerization ("MIP") process. The MIP process includes polymerization of monomeric styrene with PVP in the presence of the indicator. The polymer may then be cured and extracted using vacuum. The resultant polymer includes an active site behind a molecular cavity that is configured to bind to the indicator.

The sensing material 114 may be coated, applied to, or otherwise in operable connection to a transducer 116. One suitable transducer 116 may include graphene and single-wall carbon nanotubes ("SWNT"). Such transducers 116 are nanoscale, ultrasensitive, have a low power consumption, and are highly selective. When coupled with the highly selective sensing material 114, the assembled EB sensor 42, 96 may be used to detect sub-parts per billion level organic vapors.

According to one embodiment of the present invention, SWNTs or graphene may be dispersed in PVP or PVP-PS, and by using a solution casting process, form a network or mesh of interdigitated electrodes ("IDE"). The IDE configuration enables effective electric contact between SWNTs and the electrodes while providing large surface area for vapor adsorption. Such relatively simple fabrication is important in developing inexpensive, chemiresistor sensors that may be economically implemented.

Figure 7:
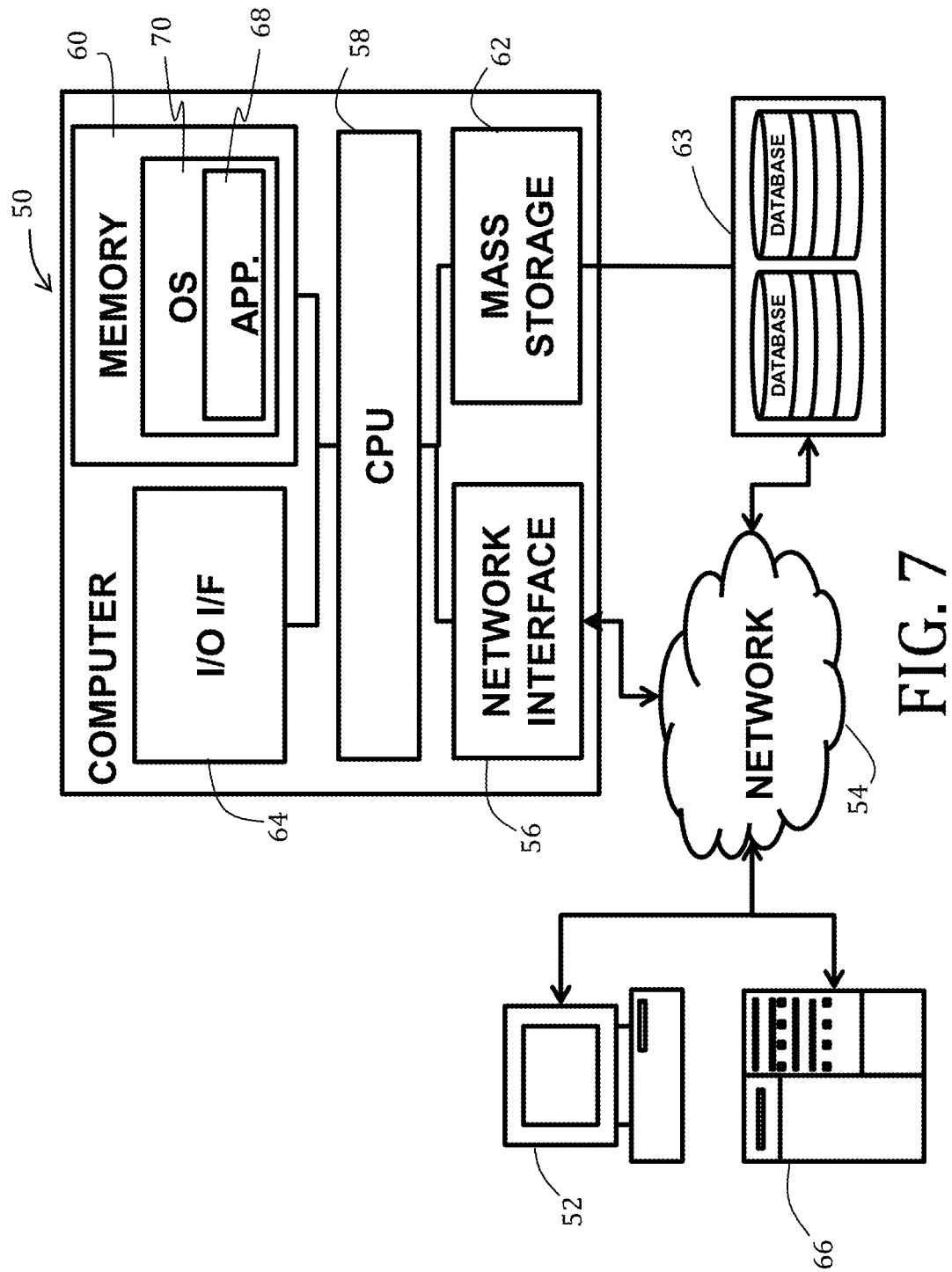
FIG. 7 is a schematic representation of a computer suitable for use with an exhalation sensor according to various embodiments of the present invention.

The EB sensor 42, 96 (FIGS. 4 and 6B) (with one or more of the carbon dioxide sensor 90, the oxygen sensor 92, and the mass flow sensor 94 of FIG. 6B) may be operably coupled to a computer 50. With reference to FIG. 7, the details of such computer 50 for operating the EB sensor 42 are described. The computer 50 that is shown in FIG. 7 may be considered to represent any type of computer, computer system, computing system, server, disk array, or programmable device such as multi-user computers, single-user computers, handheld devices, networked devices, or embedded devices, etc. The computer 50 may be implemented with one or more networked computers 52 using one or more networks 54, e.g., in a cluster or other distributed computing system through a network interface 56. The computer 50 will be referred to as "computer" for brevity's sake, although it should be appreciated that the term "computing system" may also include other suitable programmable electronic devices consistent with embodiments of the invention.

The computer 50 typically includes at least one processing unit 58 (illustrated as "CPU") coupled to a memory 60 along with several different types of peripheral devices, e.g., a mass storage device 62 with one or more databases 63, an input/output interface 64 (illustrated as "I/O I/F"), and the Network Interface 56. The memory 60 may include dynamic random access memory ("DRAM"), static random access memory ("SRAM"), non-volatile random access memory ("NVRAM"), persistent memory, flash memory, at least one hard disk drive, and/or another digital storage medium. The mass storage device 62 is typically at least one hard disk drive and may be located externally to the computer 50, such as in a separate enclosure or in one or more networked computers, one or more networked storage devices (including, for example, a tape or optical drive), and/or one or more other networked devices 66 (including, for example, a server).

The CPU 58 may be, in various embodiments, a single-thread, multi-threaded, multi-core, and/or multi-element processing unit (not shown) as is well known in the art. In alternative embodiments, the computer 50 may include a plurality of processing units that may include single-thread processing units, multi-threaded processing units, multi-core processing units, multi-element processing units, and/or combinations thereof as is well known in the art. Similarly, the memory 60 may include one or more levels of data, instruction, and/or combination caches, with caches serving the individual processing unit or multiple processing units (not shown) as is well known in the art.

The memory 60 of the computer 50 may include one or more Applications 68 (illustrated as "APP."), or other software program, which are configured to execute in combination with the Operating System 70 (illustrated as "OS") and automatically perform tasks necessary for operating the receiving and analyzing data from the one or more sensors (the EB sensor 42, 96, the carbon dioxide sensor 90, the oxygen sensor 92, and the mass flow sensor 94) with or without accessing further information or data from the database(s) 63 of the mass storage device 62.

Those skilled in the art will recognize that the environment illustrated in FIG. 7 is not intended to limit the present invention. Indeed, those skilled in the art will recognize that other alternative hardware and/or software environments may be used without departing from the scope of the invention.

Referring now to FIG. 7, with continued reference to FIGS. 3-6A, a method of using the EB sensor 42, 96 which may be conducted by way of the computer 50 of FIG. 7, in accordance with an embodiment of the present invention is shown. At start, there is a determination as to whether altitude is such that EB should be monitored (Decision Block 74). While the illustrated method 72 begins with a determination as to whether the pilot is flying at a high altitude (Decision Block 74), it would be readily understood by those skilled in the art having the benefit of the disclosure made herein that such initial determination need not be so limited. Instead, the determination may be based on elevation (such as applied to mountain climbers), ocean depth (such as applied to deep sea divers), and so forth. In any event, if the determination is negative ("No" branch of Decision Block 74), then the process may end. Otherwise, ("Yes" branch of Decision Block 74), then a feedback loop may begin.

Within the feedback loop, the EB sensor 42, 96 may be used to monitor EB for the indicators (Block 76). While monitoring, a determination as to whether an indicator is detected is made (Decision Block 78). Such indicator detection may include criteria, such as no indicator present, a threshold level of one or more indicator, a sequential order of indicator detection, and so forth. Nonetheless, if no indicator is detected or the criteria for indicator detection is not achieved ("No" branch of Decision Block 78), then the process returns to monitoring EB (Block 76). If indicator is present, criteria is met, or both ("Yes" branch of Decision Block 78), then the computer 50 (FIG. 7) may transmit an instruction to the oxygen supply system to increase oxygen content (Block 80) to the pilot by way of the breathing hose 32 and inhalation valve port 30. Oxygen content increase may be incremental, that is step-wise increased, with each determination that indicator is detected ("Yes" branch of Decision Block 78). Alternatively, oxygen flow may be initiated if not previously initiated. Alternatively still, an initial bolus of oxygen flow may be provided and followed with lower oxygen flow.

Regardless of the manner by which oxygen flow is increased, the process returns to determine whether monitoring is required (as illustrated, whether the pilot is flying at a high-altitude in Block 74). According to other embodiments, such as is illustrated by the dashed line, the process may return to further monitor EB for indicators (Block 76).

Figure 9:
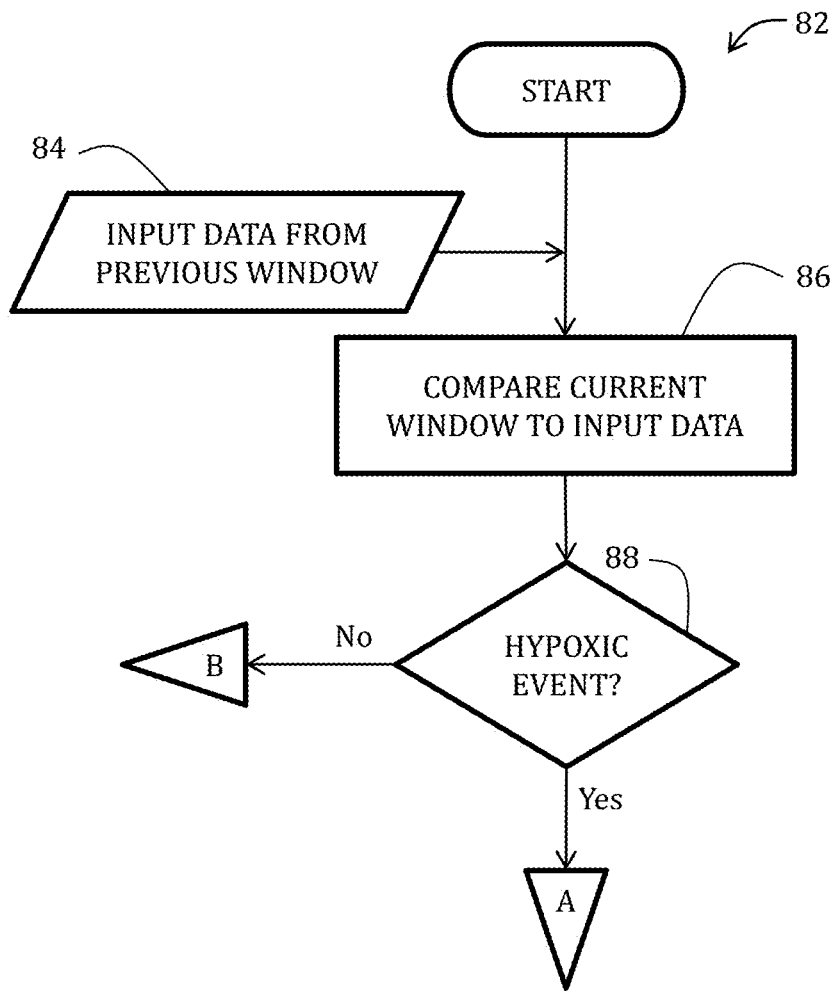
FIGS. 8 and 9 are flowcharts illustrating methods of using an exhalation sensor according to embodiments of the present invention.
Figure 8:
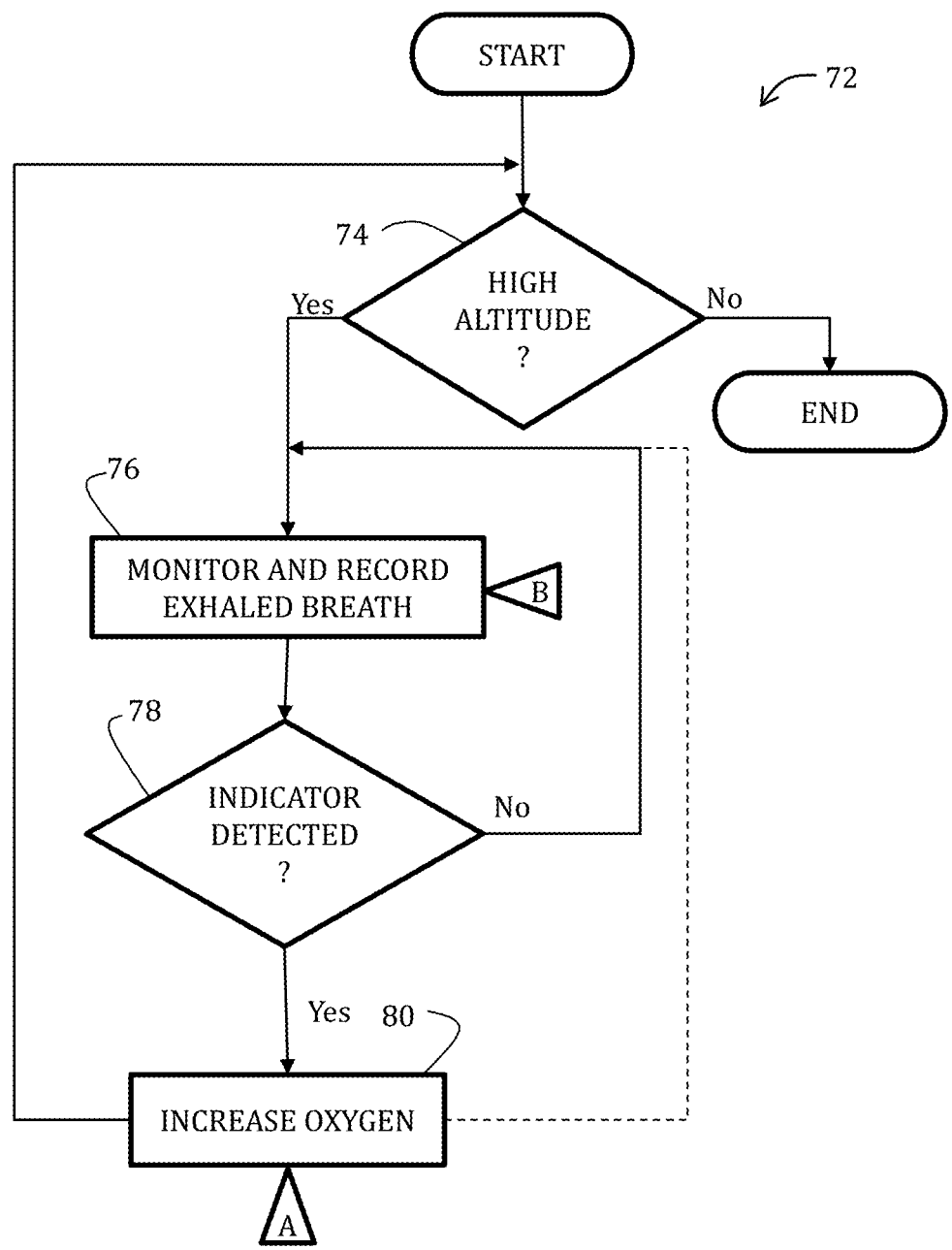
Figure 10:
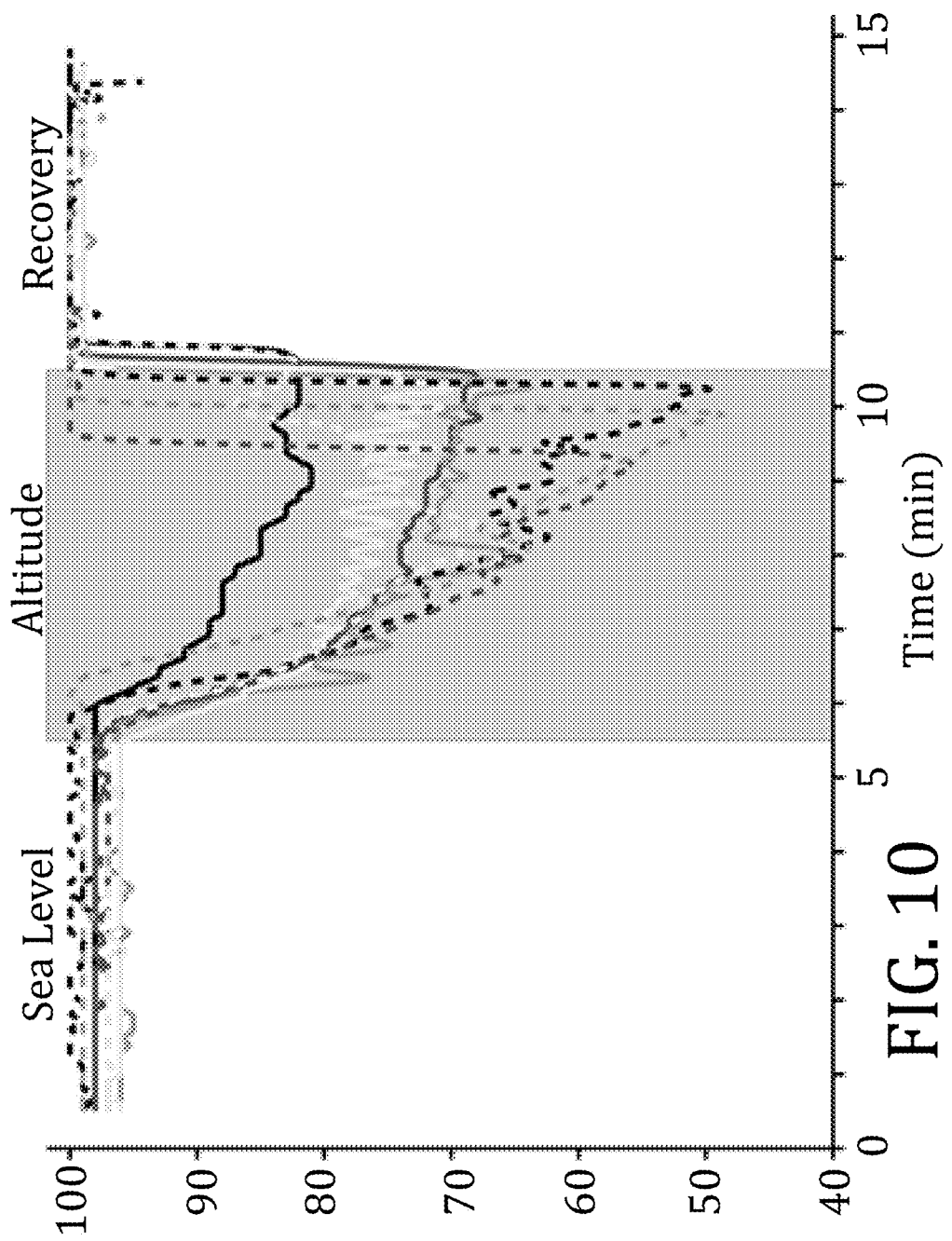
FIGS. 10-12 are graphical representations of experimental data.
Figure 11:
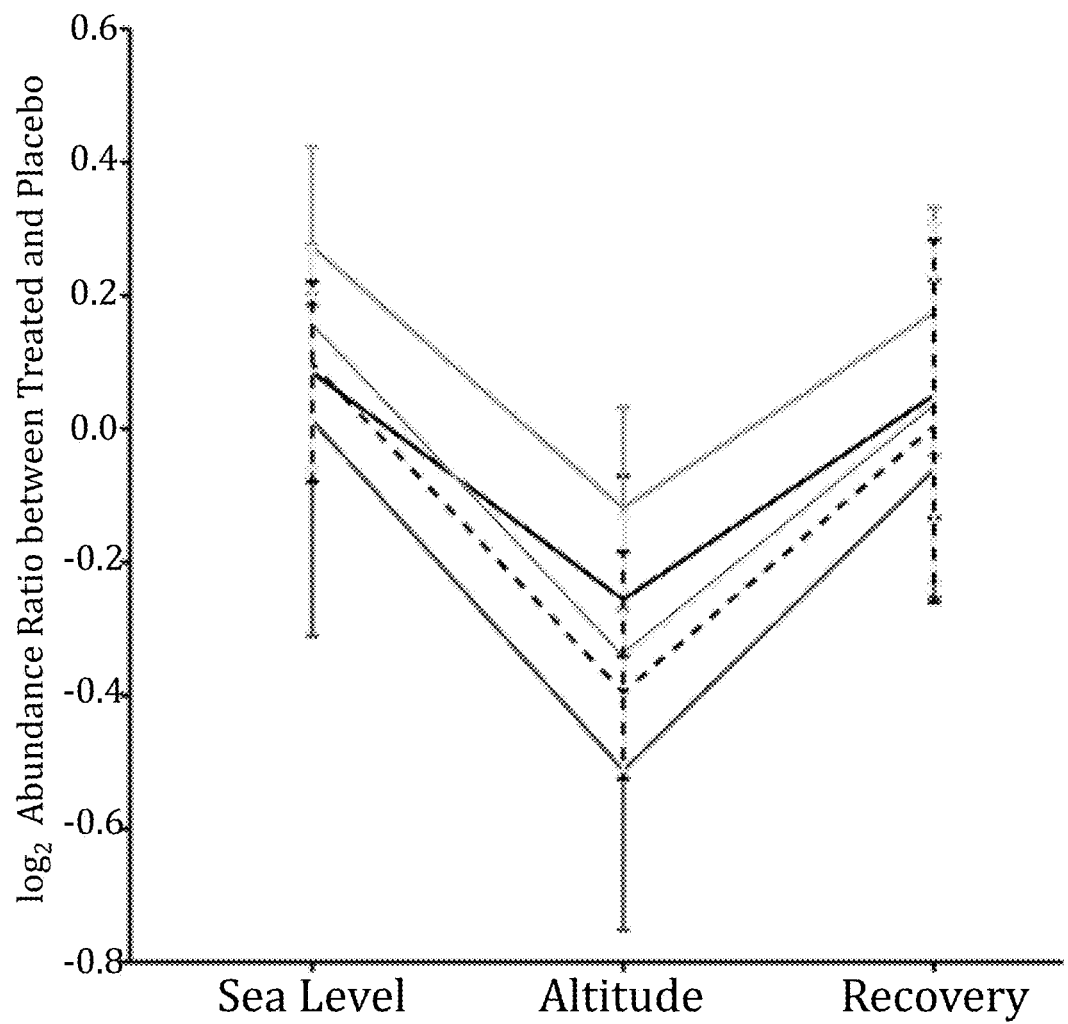
Figure 12:
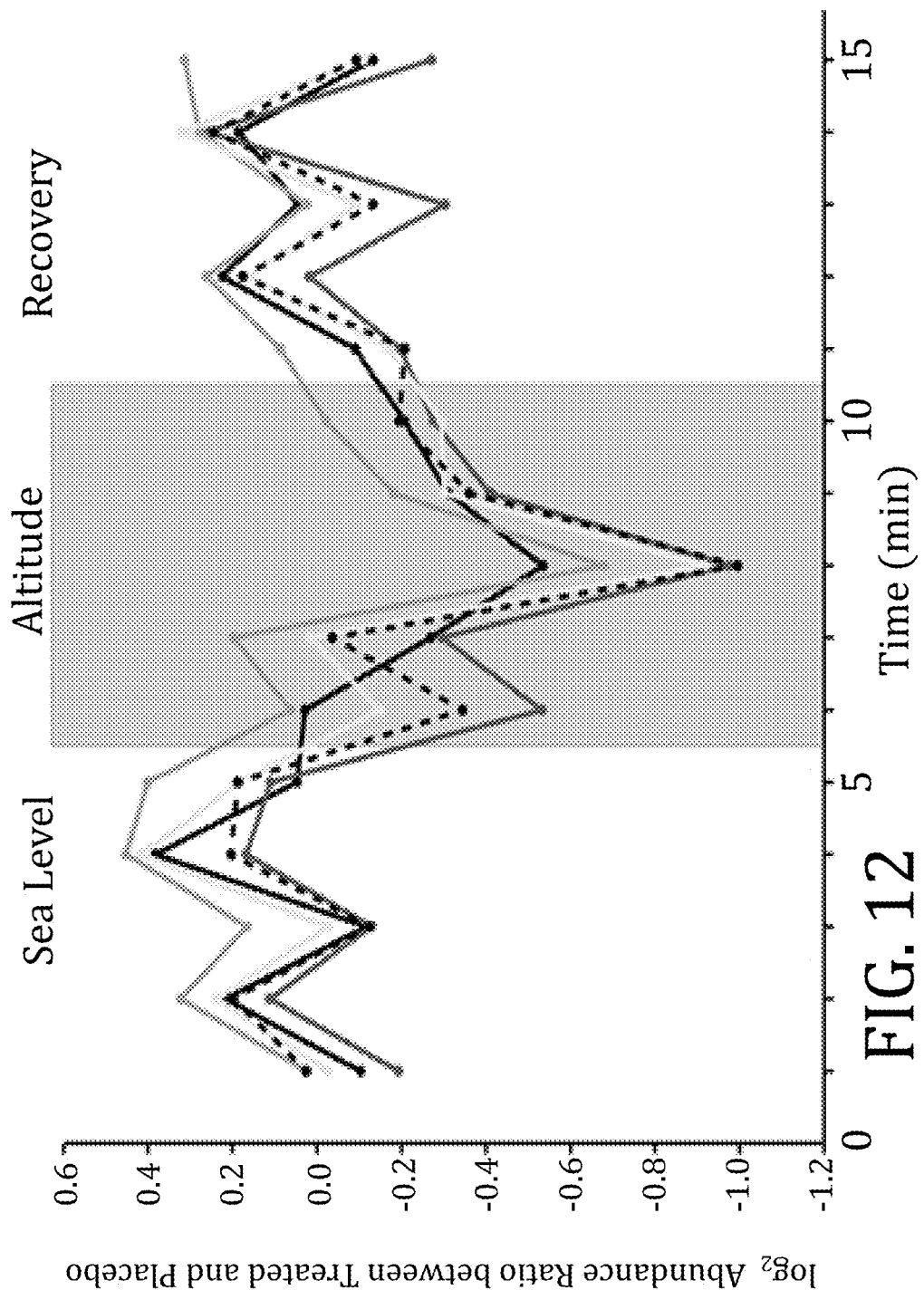

Referring now to FIG. 9, further details of a method 82 of determining presence of indicators according to an embodiment of the present invention are shown. While not specifically shown, detection data of the indicators during high altitude flight (Block 74, FIG. 8) may be recorded and stored. Data from a current data/time window are compared to input data (Block 84) from a previous time window (Block 86). According to some embodiments, the previous time window may comprise an immediately previous 3 min of recorded data. According to other embodiments, the previous time window may comprise an immediately previous 1 min, 2 min, 4 min, or 5 min of recorded data. A hypoxic event may be determined ("Yes" branch of Decision Block 88), according to an embodiment of the present invention, when a biomarker content average is greater than 0.5 of a threshold value. Reporting confidence may be proportional to 1 min an average correlation between biomarkers. If the threshold value is not approached ("No" branch of Decision Block 88), then the process may proceed to continue monitoring (Block 76, FIG. 8).

The following examples illustrate particular properties and advantages of some of the embodiments of the present invention. Furthermore, these are examples of reduction to practice of the present invention and confirmation that the principles described in the present invention are therefore valid but should not be construed as in any way limiting the scope of the invention.

EXAMPLE

Volunteer subjects were placed in a modified flight mask in line with a Reduced Oxygen Breathing Device to simulate atmospheric oxygen ($O_2$) content for altitudes up to 34,000 feet. The simulated flight profiles included three, five-min stages in sequential order: (1) sea level, (2) altitude up to 25,000 feet or sea level (as placebo), and (3) recovery (100% oxygen). Exhaled breath was collected, serially, using a Logistically-Enabled Sampling System-Portable ("LESS-P") (Signature Science, LLC, Austin, Tex.). Each sample was acquired on individual Tenax TA TD tubes of LESS-P, every min of an exposure time with a flow rate of 200 mL/min. After acquisition was complete, all samples were capped with brass/PTFE caps and stored at 4° C. until analyzed.

All sorbent tubes were thermally desorbed onto a TD-100 thermal desorber (Markes International, Ltd., Llantrisant, Wales, UK) and analyzed on a Trace Ultra-ISQ gas chromatograph in line with a single quadruple mass spectrometer (Thermo Fischer Scientific, Waltham, Mass.). Thermal desorption and GC-MS analysis of sample tubes were conducted according to conventional practices. Briefly, thermal desorption was carried out at 310° C., over 10 min. Trap settings were: flow path temperature 160° C., trap flow rate 50 mL/min, trap purge time 1 min, trap low temperature of 25° C., trap high trap temperature 315° C., trap heating rate 40° C./s, and post trap split 3.5:1.

TO-14A internal standards, bromocholoromethane, 4-bromofluorobenzene, chlorobenzene-d5, and 1,4-difluorobenzene, were applied automatically to the sorbent tube by the Markes TD-100 prior to thermal desorption (25 ppm, Linde Gas North America, Stewartsville, N.J.). GC separations were carried out on a Restek Rxi-624Sil GC column (60 m×0.32 mm ID×1.80 µm df), with a constant flow of helium (2 mL/min), over a temperature range of 40° C. to 240° C., at an increase of 10° C./min with a 20 min hold time at the maximum temperature (Bellefonte, Pa.). Mass spectral analysis was carried out via electron impact ionization at 70 eV with an ion source of 275° C. while scanning over a 35 m/z to 300 m/z range every 0.154 seconds. Data was acquired using the Thermo Scientific Trace finder EFS software package (v. 3.0). Raw data file conversion from *.RAW to *.CDF occurred using the File Conversion tool as part of the Xcalibur software package (v. 3.0, Thermo Scientific).

Data pre-processing (i.e., baseline correction, registration, and alignment) was performed using the Metabolite Differentiation and Discovery Lab software developed by/for the United States Air Force (do we have a contract number?). All pre-processed peak sets were exported for statistical analysis.

Statistical analyses were performed within MatLab© software environment (v. R2013a, MathWorks, Natick, Mass.). Quantile normalization was applied to LESS-P samples to correct for sample-to-sample total intensity variations that may be associated with collection volume differences. After normalization, a loge transformation was applied to force Gaussian distribution behavior. Samples within each altitude simulation were averaged per subject, and finally, the loge ratio between hypoxia and placebo was assessed using a linear statistical model or analysis of variance.

TABLE 1

| Subject | Line style | min($SpO_2$) (%) |
|---------|------------|------------------|
| 1 | —— | 81 |
| 2 | ········ | 67 |
| 3 | ········ | 63 |
| 4 | ▬▬▬ | 69 |
| 5 | – – – – | 48 |
| 6 | ···· ···· ···· | 55 |
| 7 | ··· ··· | 47 |
| 8 | ▬▬▬▬ | 68 |

TABLE 2

| Compound | Line Style | m/z |
|----------|------------|-----|
| Pentanal | —— | 41 |
| 4-Butyrolactone | ········ | 56 |
| 2-Pentanone | ········ | 43 |
| 2-Hexanone | ---------- | 43 |
| 2-Heptanone | – – – – | 58 |
| 2-Cyclopenten-1-one | | 82 |

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A method of detecting hypoxia, the method comprising:
   measuring, with a sensor configured to be exposed to breath being exhaled, at least one indicator for hypoxia selected from a group consisting of pentanal, 2-pentanone, 2-hexanone, 2-heptanone, 2-cyclopenten-1-one, and 4-butyrolactone; and with a processor, determining an amount of the at least one indicator and comparing the amount to a threshold level to indicate hypoxia.

2. The method of claim 1, further comprising:
comparing the amount measured of the at least one indicator relative to an amount measured of another of the at least one indicators.

3. The method of claim 1, wherein measuring the at least one indicator includes comparing a present amount of the at least one indicator to a previous amount of the at least one indicator.

4. The method of claim 3, wherein the previous amount is an average concentration measured during a time window ranging from 1 min to 5 min.

5. The method of claim 1, further comprising:
measuring, with another sensor configured to be exposed to the exhaled breath, at least one of an oxygen content, a carbon dioxide content, and a mass flow.

6. The method of claim 1, wherein the sensor is a molecular imprint polymerization based sensor.

7. A method of detecting hypoxia in a pilot flying at high-altitude, the method comprising:
measuring, with a sensor configured to be exposed to the exhaled breath of the pilot, at least one indicator of hypoxia, the at least one indicator selected from the group consisting of pentanal, 2-pentanone, 2-hexanone, 2-heptanone, 2-cyclopenten-1-one, and 4-butyrolactone;

with a processor, comparing the measured amount of the at least one indicator to a threshold level to indicate hypoxia; and if the measured amount of the at least one indicator is greater than the threshold level, increasing a flow of oxygen to the pilot.

8. The method of claim 7, further comprising:
decreasing the flow of oxygen to the pilot after the measured amount of the at least one indicator is less than the threshold level.

9. The method of claim 7, wherein measuring the at least one indicator includes comparing a present amount of the at least one indicator to a previous amount of the at least one indicator.

10. The method of claim 9, wherein the previous amount is an average concentration measured during a time window ranging from 1 min to 5 min.

11. The method of claim 7, further comprising:
measuring, with another sensor configured to be exposed to the exhaled breath, at least one of an oxygen content, a carbon dioxide content, and a mass flow.

12. The method of claim 7, wherein the sensor is a molecular imprint polymerization based sensor operably coupled to a flight mask of the pilot.

* * * * *